US012591953B2

(12) United States Patent
Chiu

(10) Patent No.: US 12,591,953 B2
(45) Date of Patent: Mar. 31, 2026

(54) IMAGE REASSEMBLY SYSTEM AND METHOD APPLIED TO MAGNETIC RESONANCE IMAGING

(71) Applicant: You-Yin Chen, New Taipei City (TW)

(72) Inventor: Feng-Mao Chiu, New Taipei City (TW)

(73) Assignee: You-Yin Chen, New Taipei City (TW)

( * ) Notice: Subject to any disclaimer, the term of this patent is extended or adjusted under 35 U.S.C. 154(b) by 278 days.

(21) Appl. No.: 18/490,829

(22) Filed: Oct. 20, 2023

(65) Prior Publication Data

US 2024/0273680 A1     Aug. 15, 2024

(30) Foreign Application Priority Data

Feb. 9, 2023   (TW) ................................. 112104554

(51) Int. Cl.
| | |
|---|---|
| *G06T 5/50* | (2006.01) |
| *A61B 5/055* | (2006.01) |
| *A61B 5/08* | (2006.01) |
| *A61B 5/113* | (2006.01) |

(52) U.S. Cl.
CPC ................ *G06T 5/50* (2013.01); *A61B 5/055* (2013.01); *A61B 5/0816* (2013.01); *A61B 5/1135* (2013.01); *G06T 2207/10088* (2013.01)

(58) Field of Classification Search
CPC ............. G06T 5/50; G06T 2207/10088; A61B 5/0816; A61B 5/055; A61B 5/1135; A61B 5/113
See application file for complete search history.

(56) References Cited

PUBLICATIONS

Krishnamoorthy, Guruprasad et al. Free breathing 2D Radial Cine MRI with Respiratory Auto calibrated Motion Correction (RAMCO). Magnetic resonance in medicine 89.3 (2023): 977-989. Web. (Year: 2022).*
Ludwig, Juliane et al. Pilot Tone-Based Prospective Correction of Respiratory Motion for Free-Breathing Myocardial T1 Mapping. Magma (New York, N.Y.) 36.1 (2023): 135-150. Web. (Year: 2022).*

* cited by examiner

*Primary Examiner* — John R Wallace

(57)     ABSTRACT

The present invention discloses an image reassembly system, method, and computer-readable storage medium applicable to magnetic resonance imaging (MRI). The image reassembly method includes a pre-scanning process and a formal scanning process. In the pre-scanning process, a self-modeled profile related to a subject is acquired. The self-modeled profile is used for calibrating a free-breathing signal obtained during the formal scanning. A reassembled image volume is generated by selecting required corresponding image volume data through the establishment of a reassembled reference state table.

9 Claims, 11 Drawing Sheets obtaining the pre-scan breathing curve and the navigator profile associated with the subject    S11 correcting the time difference of the pre-scan breathing curve according to the navigator profile    S12 generating the calibrated respiratory waveform    S13 differentiating the pre-scan
breathing curve into multiple
separate respiratory waveforms — S131 adjusting each respiratory
waveform to the average
respiratory waveform with the
same sequence length — S132 averaging the respiratory
waveforms with the same
sequence length to generate the
calibrated respiratory waveform — S133

W011   W012   W013   W014   W015   W016

W01

W031   W032   W033   W034   W035   W036

W03

I01

IMAGE REASSEMBLY SYSTEM AND METHOD APPLIED TO MAGNETIC RESONANCE IMAGING

CROSS REFERENCE TO RELATED APPLICATIONS

This Non-provisional application claims priority under 35 U.S.C. § 119(a) on patent application Ser. No. 11/210,454 filed in Republic of China on Feb. 9, 2023, the entire contents of which are hereby incorporated by reference.

BACKGROUND

1. Technical Field

The present invention relates to a medical imaging system and method, in particular to an image reassembly system, method, and a computer-readable storage medium applied to magnetic resonance imaging.

2. Description of Related Art

Magnetic resonance imaging (MRI) is a non-invasive technique used to visualize cross-sectional anatomical structures of soft tissues without radiation exposure.

Although MRI provides high-precision images necessary for disease diagnosis, it has certain technical limitations, one of which is sensitivity to motion. When humans breathe, organs also move with the motion of the diaphragm. Imaging organs that move with respiration using MRI devices results in motion artifacts, as illustrated in FIG. 1, where the imaging position constantly changes, particularly indicated by the arrow in the liver image.

To mitigate motion artifacts, it is typically recommended for subjects to hold their breath and remain still during image acquisition. However, breath-holding is a technique that may not be suitable for all subjects, especially those with health issues. Therefore, it is an important subject to improve the above-mentioned issue and enable subjects to obtain clear images while breathing freely.

SUMMARY OF THE INVENTION

In view of the foregoing, an object of the present invention is to provide an image reassembly system, an image reassembled method, and a computer-readable storage medium, which are applied to magnetic resonance imaging (MRI). The system, method, and storage medium aim to acquire clear images in the state of free breathing.

To achieve the above, an image reassembly method applied to magnetic resonance imaging, which includes a pre-scanning process and a formal scanning process. The pre-scanning process includes the following steps (A) to (D): (A) Obtaining a pre-scan breathing curve associated with a subject from a breath detector; (B) Obtaining a navigator associated with a target tissue of the subject along the sagittal direction while obtaining the breathing curve profile; (C) Correcting a time difference of the pre-scan breathing curve according to the navigator profile; (D) Generating a calibrated respiratory waveform according to the average of the pre-scan breathing curve. The formal scanning process includes the following steps (E) to (I): (E) Obtaining a free-breathing curve associated with the subject from the breath detector, which has a plurality of respiratory waveforms; (F) Utilizing the calibrated respiratory waveform to refill the respiratory waveforms of the free-breathing curve for generating a free-breathing signal; (G) Generating a reassembled reference state table according to the free-breathing signal; (H) Obtaining a plurality of image volume data of the target tissue of the subject according to the reassembled reference state table; and (I) Retrieving the relevant image volume data based on the reassembled reference state table to generate a reassembled image volume.

In one embodiment, a time difference between the pre-scan breathing curve and the navigator profile is obtained by aligning the pre-scan breathing curve and the navigator profile through peak detection.

In one embodiment, in the pre-scanning process, the step to obtain the calibrated respiratory waveform includes: segmenting the pre-scan breathing curve into a plurality of respiratory waveforms; adjusting each respiratory waveform to the same length; and averaging the adjusted length respiratory waveforms to derive the calibrated respiratory waveform.

In one embodiment, the respiratory waveforms are differentiated through a peak detection of the pre-scan breathing curve.

In one embodiment, each respiratory waveform is adjusted in length by interpolation.

In one embodiment, after obtaining the free-breathing curve, it further includes adjusting the timing of the free-breathing curve according to the time difference obtained by the pre-scanning process.

In one embodiment, in the formal scanning process, it further includes normalizing the amplitude of each respiratory waveform of the free-breathing curve to a range of 0 to 1.

In one embodiment, the image volume data is a K-space volume.

In one embodiment, the reassembled image volume includes a plurality of consecutive excitation points corresponding to the reassembled reference state table, wherein the number of excitation points is fewer than three times the count of excitation points required for composing a single reassembled image volume.

Additionally, to achieve the above object, an image reassembly system for reassembling an image associated with a target tissue includes a computer device configured to perform a pre-scanning process and a formal scanning process. The pre-scanning process includes the following steps (A) to (D): (A) Obtaining a pre-scan breathing curve associated with a subject from a breath detector; (B) Obtaining a navigator associated with a target tissue of the subject along the sagittal direction while obtaining the breathing curve profile; (C) Correcting a time difference of the pre-scan breathing curve according to the navigator profile; (D) Generating a calibrated respiratory waveform according to the average of the pre-scan breathing curve. The formal scanning process includes the following steps (E) to (I): (E) Obtaining a free-breathing curve associated with the subject from the breath detector, which has a plurality of respiratory waveforms; (F) Utilizing the calibrated respiratory waveform to refill the respiratory waveforms of the free-breathing curve for generating a free-breathing signal; (G) Generating a reassembled reference state table according to the free-breathing signal; (H) Obtaining a plurality of image volume data of the target tissue of the subject according to the reassembled reference state table; and (I) Retrieving the relevant image volume data based on the reassembled reference state table to generate a reassembled image volume.

Furthermore, to achieve the above, a computer-readable storage medium contains a computer-executable instruction for reorganizing image data associated with a target tissue.

When the computer device executes the instructions, the computer device is configured to perform a pre-scanning process and a formal scanning process. The pre-scanning process includes the following steps (A) to (D): (A) Obtaining a pre-scan breathing curve associated with a subject from a breath detector; (B) Obtaining a navigator associated with a target tissue of the subject along the sagittal direction while obtaining the breathing curve profile; (C) Correcting a time difference of the pre-scan breathing curve according to the navigator profile; (D) Generating a calibrated respiratory waveform according to the average of the pre-scan breathing curve. The formal scanning process includes the following steps (E) to (I): (E) Obtaining a free-breathing curve associated with the subject from the breath detector, which has a plurality of respiratory waveforms; (F) Utilizing the calibrated respiratory waveform to refill the respiratory waveforms of the free-breathing curve for generating a free-breathing signal; (G) Generating a reassembled reference state table according to the free-breathing signal; (H) Obtaining a plurality of image volume data of the target tissue of the subject according to the reassembled reference state table; and (I) Retrieving the relevant image volume data based on the reassembled reference state table to generate a reassembled image volume.

The detailed technology and preferred embodiments implemented for the subject invention are described in the following paragraphs accompanying the appended drawings for people skilled in this field to well appreciate the features of the claimed invention.

BRIEF DESCRIPTION OF THE DRAWINGS

The parts in the drawings are not necessarily drawn to scale, the emphasis instead being placed upon clearly illustrating the principles of at least one embodiment. In the drawings, like reference numerals designate corresponding parts throughout the various diagrams, and all the diagrams are schematic.

DETAILED DESCRIPTION

Figure 2:
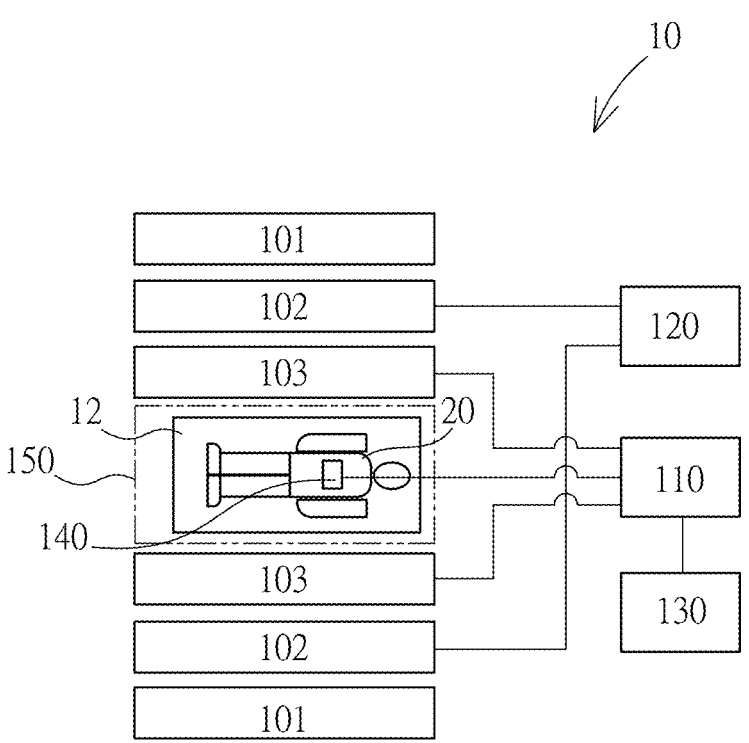
FIG. 2 is a schematic structural block diagram showing an MRI apparatus according to an embodiment of the invention.

FIG. 2 is a schematic diagram of the structure of the MRI apparatus 10, and also shows a schematic diagram of the subject 20 placed on a carrier 12 and carried in the MRI apparatus 10.

The MRI apparatus 10 has a static magnetic field magnet 101, a gradient coil 102, an RF coil 103, a transceiver module 110, a power supplying module 120, and a processing module 130.

The static magnetic field magnet 101 generates a static magnetic field. The gradient coil 102 generates a gradient magnetic field. The gradient coil 102 is connected with the power supply module 120, and a desired gradient magnetic field is formed in a space within an inspection area 150 by changing the current flowing through the gradient coil 102. The RF coil 103 sends transmission pulses to the subject 20 of the inspection area 150 and receives a reception pulse from the subject 20. The transceiver module 110 outputs a measurement signal to the processing module 130 according to the reception pulses. The processing module 130 performs processing including, but not limited to, time shift, signal conversion, image construction, etc., according to the measurement signals.

In addition, a body motion monitoring module 140 that collaborates with the MRI apparatus 10 is capable of detecting a plurality of body motion information from the subject 20. In this embodiment, the body motion monitoring module 140 is, for example but not limited to, a breath detector, which can detect and output a breathing state including waveforms, signals, or data of the subject 20.

An image reassembly method, as per an embodiment of the invention, is employed in the MRI technique and comprises a pre-scanning process and a formal scanning process. Both the pre-scanning and formal scanning processes are conducted on the subject while they are in a free-breathing state, eliminating the need for the subject to hold their breath.

Figure 3:
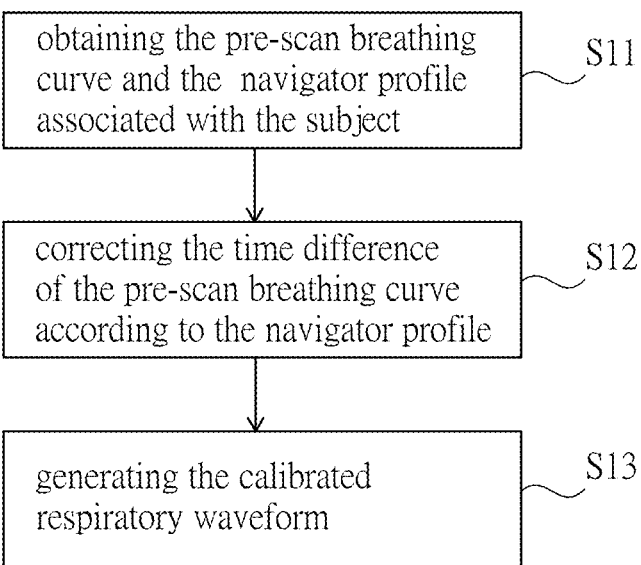
FIG. 3 is a flowchart showing a pre-scanning process applied in the image reassembled method according to the embodiment of the invention.

FIG. 3 is a flowchart of the pre-scanning process, comprising steps S11 to S13.

In step S11, a breath detector obtains a pre-scan breathing curve associated with the subject and simultaneously acquires a navigator profile linked to a specific target tissue within the sagittal plane of the subject, from a navigator. The breath detector, such as a respiratory belt, is utilized for this purpose. The navigator employs the navigation echo method for 2D dynamic scanning. Additionally, in this embodiment, the liver serves as the exemplar target tissue; however, this is not restrictive. Other organs and tissues such as the stomach, bladder, or lungs can also be considered, with particular suitability for the abdominal cavity.

Figure 4:
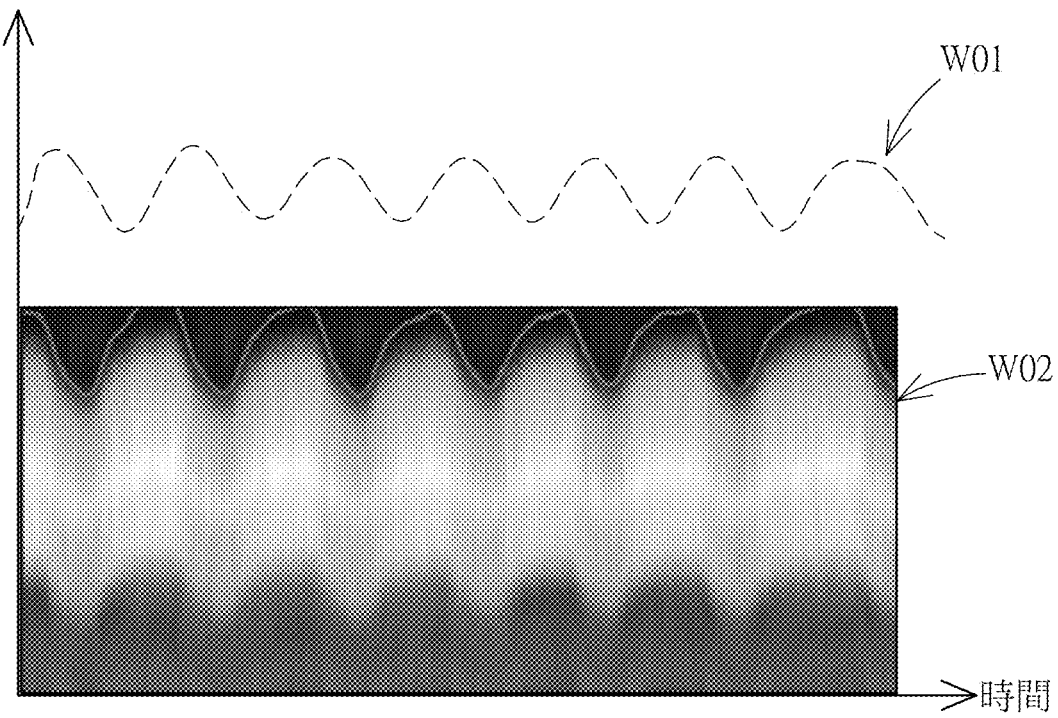
FIG. 4 is a schematic diagram showing a timing relationship between a pre-scan breathing curve and a navigator profile received by the image reassembled method according to the embodiment of the invention.

FIG. 4 presents a schematic depiction of the temporal correlation between the pre-scan breathing curve W01 acquired by the breath detector and the navigator profile W02 generated by the navigator. As illustrated in FIG. 4, both the pre-scan breathing curve W01 and the navigator profile W02 exhibit similar waveform patterns, but there is a specific difference in timing. Hence, step S12 is to correct the time difference of the pre-scan breathing curve W01 according to the navigator profile W02. In this embodiment, the pre-scan breathing curve W01 can be aligned with the navigator profile W02 via the peak detection (finding) process, consequently identifying the subject's end-inspiration point. However, due to potential variations between the operational approach of the breath detector and actual breathing dynamics, the pre-scan breathing curve W01 is rectified based on the navigator profile W02.

Figure 5:
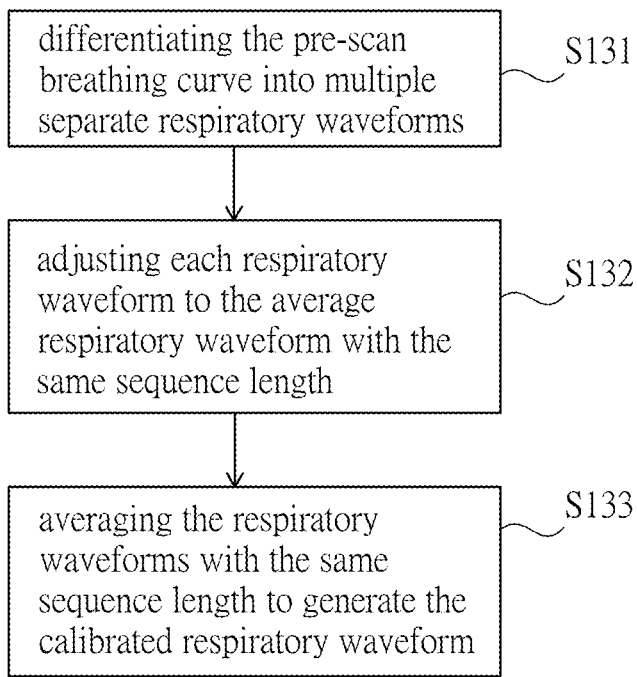
FIG. 5 shows a flowchart for generating the calibrated respiratory waveform in the pre-scanning process used in the embodiment of the invention.
Figure 6A:
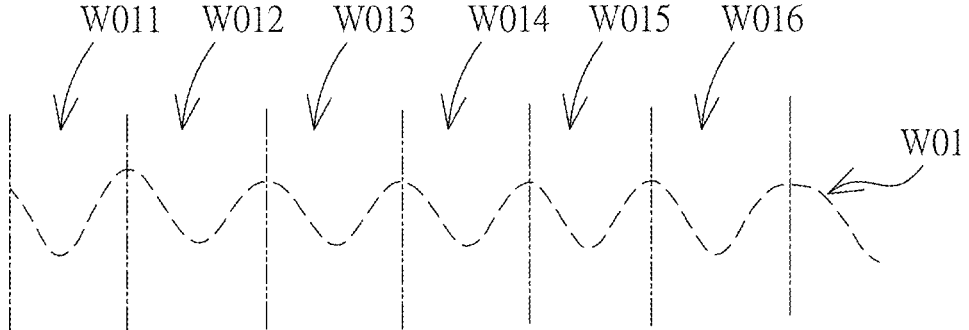
FIG. 6A is a schematic diagram showing the pre-scan breathing curve divided into a plurality of individual respiratory waveforms.
Figure 6B:
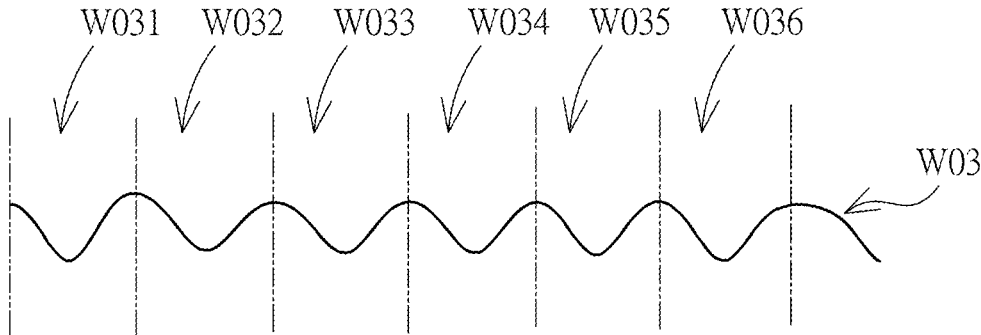
FIG. 6B is a schematic diagram showing the average of the respiratory waveform with the same sequence length in the image reassembled method according to the embodiment of the invention.
Figure 7:
FIG. 7 is a schematic diagram showing the calibrated respiratory waveform generated by the image reassembled method according to the embodiment of the invention.
Figure 8:
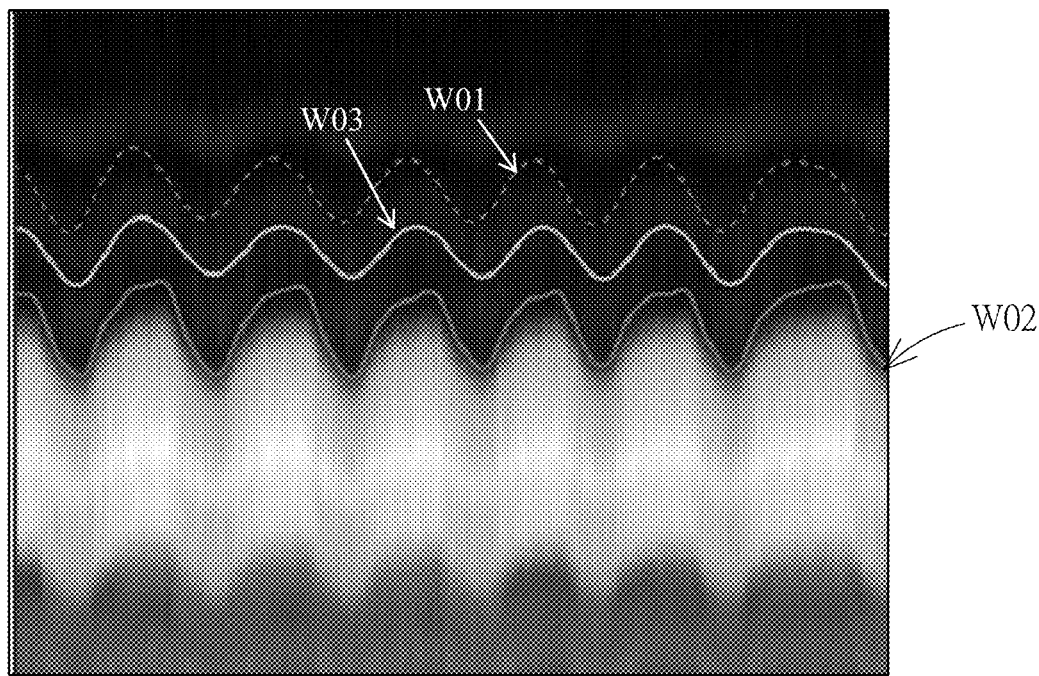
FIG. 8 is a schematic diagram showing the corresponding relationship in time series between the pre-scan breathing curve, the navigator profile, and the average respiratory waveform generated in the image reassembled method according to the embodiment of the invention.

Step S13 is to generate a calibrated respiratory waveform W04 as shown in FIG. 7 according to the pre-scan breathing curve W01. To provide further clarity, as shown in FIG. 5, step S13 also includes steps S131 to S133. In particular, within step S131, the peak detection method is employed to differentiate pre-scan breathing curve W01 into a plurality of separate respiratory waveforms W011 to W016, as illustrated in FIG. 6A. That is, the curve is composed of multiple described by a sequence. Step S132 is to use the interpolation method to adjust each respiratory waveform W011 to W016 to an average respiratory waveform W03 with the same sequence length as shown in FIG. 6B. In short, for example, the interpolation result is to adjust each respective respiratory waveforms W031 to W036 to have 128 sequences. Under this premise, for example, if a certain respiratory waveform has only 100 sequences, it will be interpolated to 128 sequences. Similarly, if a certain respiratory waveform has 135 sequences, it will also be adjusted to 128 sequences. Step S133 is to average the respiratory waveforms W031 to W036 with the same sequence length to generate a calibrated respiratory waveform W04 as shown in FIG. 7. The calibrated respiratory waveform W04 is also known as a self-modeled profile. FIG. 8 shows the corresponding relationship of the aforementioned pre-scan breathing curve W01, the navigator profile W02 and the average respiratory waveform W03 in terms of timing.

As an embodiment, assuming each breath is similar to all other breaths, the use of an average curve (the average respiratory waveform) can replace all recorded breaths. The average curve is derived from the actual liver displacement. Firstly, in each image of the two-dimensional dynamic pre-scan volume, the edge of the liver dome is detected, which forms a sequence of displacement profiles (the navigator profile) recorded continuously. Subsequently, the end-inspiration point is determined through peak detection using the displacement curve. Following that, the entire displacement curve (the pre-scan breathing curve corrected for time difference) is divided into individual breaths using peak positions. Each isolated breath sequence is then interpolated to the same length. Lastly, the self-modeled profile represents the average of all interpolated breaths.

Figure 9:
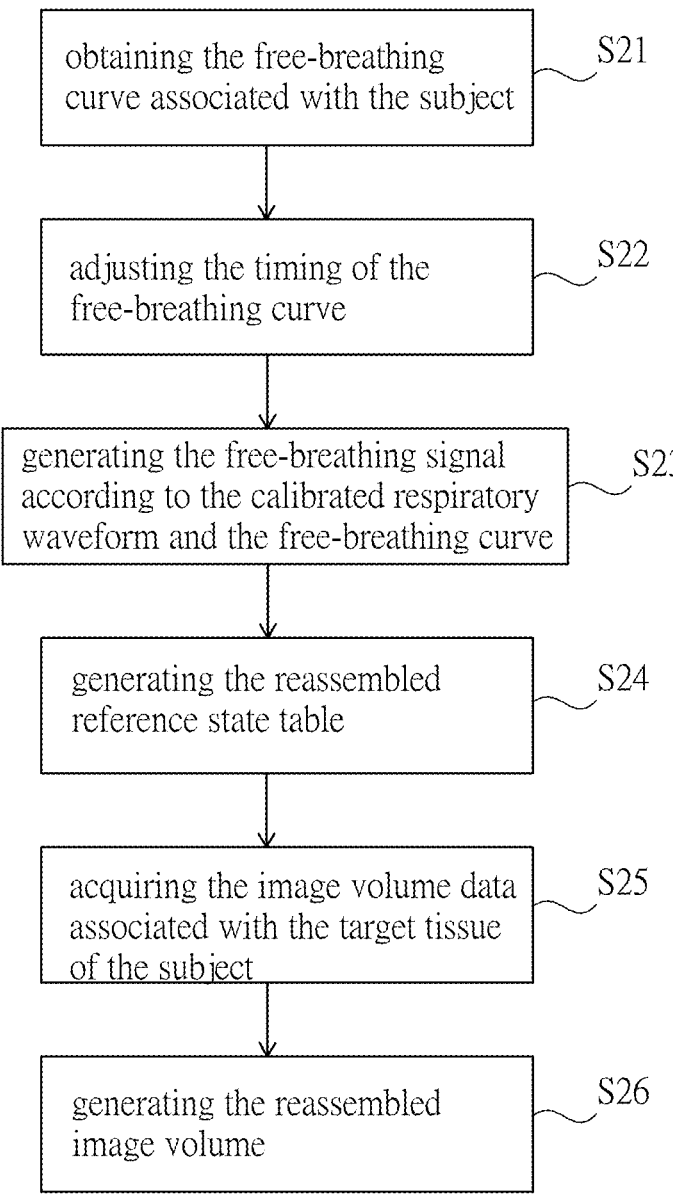
FIG. 9 is a flowchart showing a formal scanning process applied in the image reassembled method according to the embodiment of the invention.

Next, please refer to FIG. 9, after the completion of the pre-scanning process, the formal scanning process, including but not limited to steps S21 to S26, will be executed.

Step S21 is to obtain a free-breathing curve associated with the subject from the breath detector, which has multiple respiratory waveforms. Similar to the pre-scanning process, the free-breathing curve is obtained from the subject in a free-breathing state using the respiratory belt.

Figure 10:
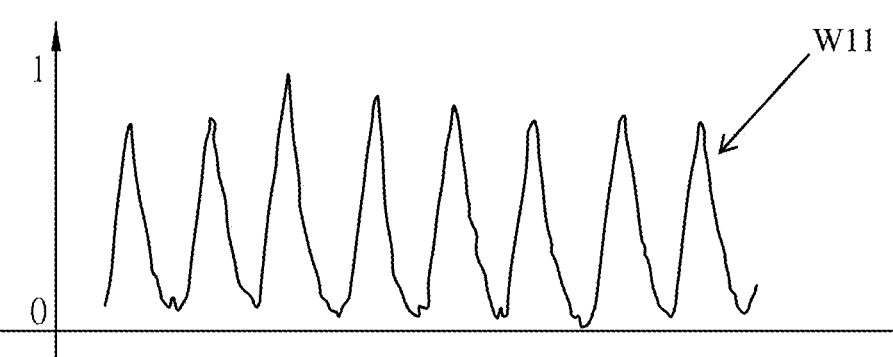
FIG. 10 is a schematic diagram showing the normalized free respiratory waveform in the image reassembled method according to the embodiment of the invention.

Step S22 involves adjusting the timing of the free-breathing curve based on the time difference obtained in the pre-scanning process and normalizing the waveform amplitude of the free-breathing curve to a range between 0 and 1 (i.e., the peaks and valleys of each waveform fall within the range of 0 to 1), resulting in the normalized free-respiratory waveform W11 as shown in FIG. 10. The waveforms obtained by the breath detector regarding respiration often exhibit drift due to various environmental factors. The normalization process described above helps mitigate the impact of such drift to some extent.

Step S23 utilizes the calibrated respiratory waveform W04 to refill the respiratory waveforms of the free-breathing curve, generating a free-breathing signal. The free-breathing signal can be in the form of signals, sequences, or waveform curves output by the respiratory belt.

Figure 11:
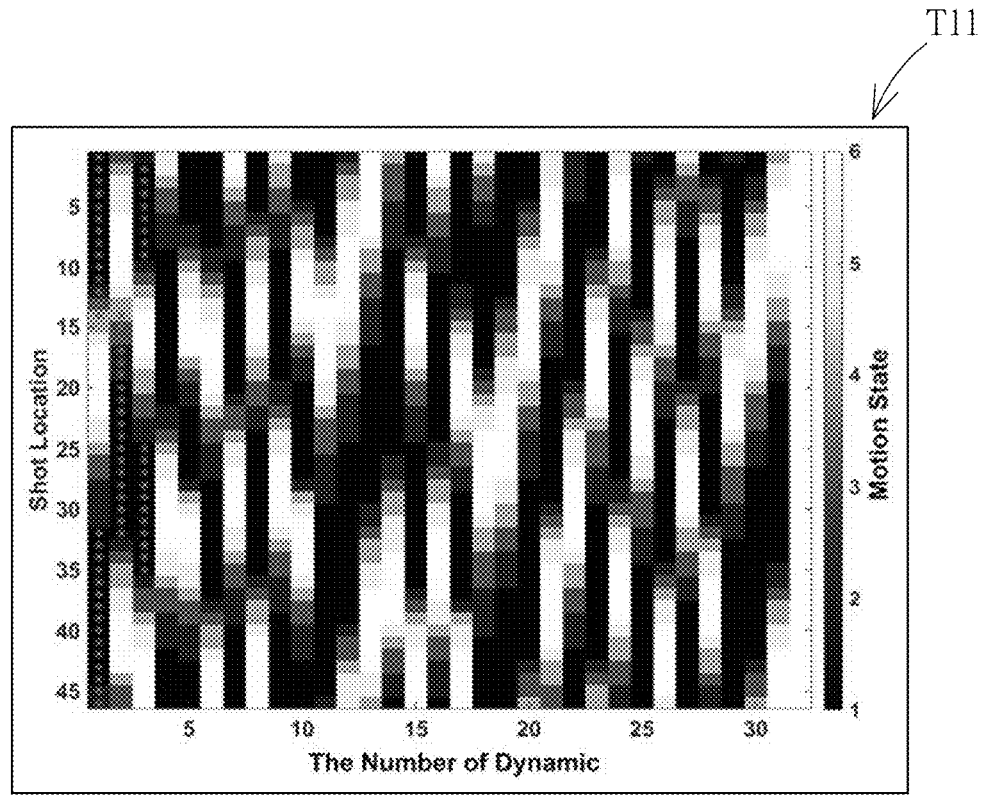
FIG. 11 is a schematic diagram showing a reassembled reference state table generated by the image reassembled method according to the embodiment of the invention.

Step S24 involves generating a reassembled reference state table T11 based on the free-breathing signal as shown in FIG. 11. In this embodiment, the respiratory motion states are categorized into six levels, where motion state 1 corresponds to the end-expiratory phase of the subject, and motion state 6 corresponds to the end-inspiratory phase. Therefore, for each respiratory motion cycle, motion states 1 to 6 are sequentially and cyclically arranged, with each motion state corresponding to an excitation point (or called as shot). In this embodiment, each row comprises 46 excitation points, and every 46 excitation points can compose a complete image associated with the target organ tissue. It should be noted, among the six levels of respiratory motion states, motion state 1 corresponds to clearer image excitation points, while motion state 6 corresponds to relatively blurred image excitation points. Furthermore, the aforementioned six motion state levels and 46 excitation points form a complete image, and the numbers are exemplary and not restrictive. They can be adaptively modified based on the capabilities of software and hardware specifications.

Step S25 is to acquire a plurality of image volume data associated with the target tissue of the subject based on the reassembled reference state table T11 generated from the free-breathing signal. The image volume data can be K space volume, for instance. In this embodiment, the image volume data, which corresponds to the aforementioned excitation points, is generated through the 4D dynamic free-breathing imaging of the MRI apparatus 10.

Figure 1:
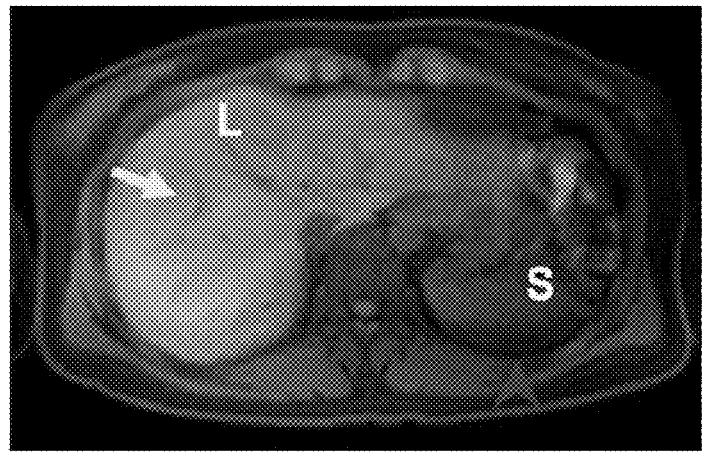
FIG. 1 is a schematic diagram showing an imaging with motion artifacts produced by an MRI apparatus of the prior art.
Figure 12:
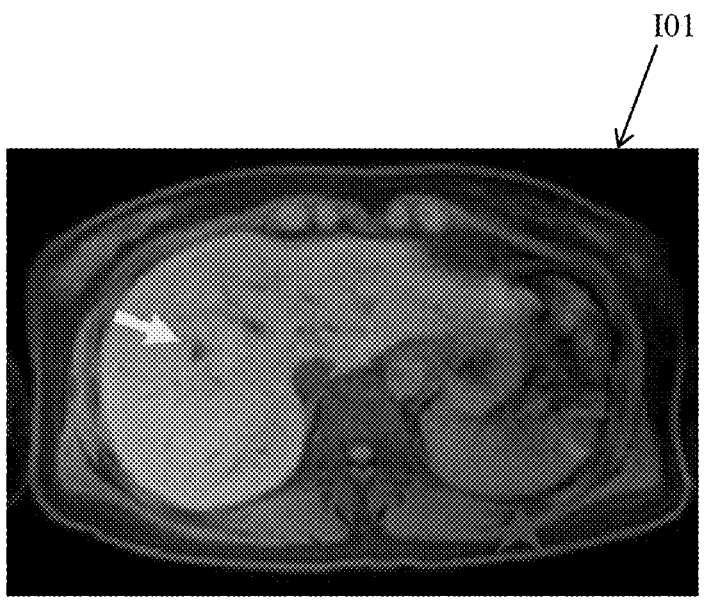
FIG. 12 is a schematic diagram showing a reassembled image volume generated by the image reassembled method according to the embodiment of the invention.

Step S26 is to extract corresponding image volume data based on the reassembled reference state table T11 to generate a reassembled image volume I01, as shown in FIG. 12. In FIG. 12, a clearer imaging contrast compared to FIG. 1 can be observed. Within the reassembled reference state table T11, each column represents excitation points contributing to the formation of image volumes, and each row represents different excitation points corresponding to the same time in the same K-space. Referring back to FIG. 11, it can be observed from the reassembled reference state table T11 that due to the fluctuations caused by respiratory motion, the number and positions of excitation points corresponding to the motion state 1 in each row are different. Therefore, in this embodiment, the reassembled image volume I01 is constructed from adjacent multi-rows of the reassembled reference state table T11. Specifically, this embodiment selects three consecutive rows, utilizing three consecutive K-space image volumes for selection and reconstruction.

However, the excitation points corresponding to the motion state 1 within the selected three consecutive rows may not always suffice for reconstructing a complete image volume. In such cases, it is possible to further relax the selection criteria to include excitation points corresponding to the motion state 2 or the motion state 3, as illustrated by the asterisk annotations in FIG. 11. Moreover, if it is not feasible to obtain an adequate number of excitation points within the selected three rows to fulfill the requirements for image volume reconstruction, expansion to four to six rows can also be considered. This expansion is primarily driven by the aim to acquire clear data, and it may be associated with the sampling frequency, with higher frequencies permitting a greater number of selected rows.

It is worth mentioning that the aforementioned K-space image volume data can be obtained by subjecting the original image volume generated by the MRI apparatus to a Fourier transform. Subsequently, following the selection of corresponding K-space image volumes, an inverse Fourier transform is applied to generate the reassembled image volume I01.

As an example, the aforementioned MRI apparatus 10 can be a 3T MRI system utilizing a 16-channel torso coil. Parameters for the two-dimensional dynamic scan include: time of repetition (TR)/time of echo (TE), 2.4/1.2 ms; flip angle, 10°; field of view (FOV), 320×320 mm$^2$; matrix size, 192×192; slice thickness, 6 millimeters (mm); number of dynamic frames, 400; sensitivity encoding (SENSE) acceleration factor, 2; number of signal averages (NSA), 1; orientation, sagittal; and a time resolution, 166 ms/frame. For the four-dimensional dynamic free-breathing imaging, parameters include: TR/TE, 2.5/1.2 ms; flip angle, 10°; FOV, 350×300×250 mm$^2$; acquisition matrix, 224×128×46; SENSE acceleration factor, 2; acceleration direction, anterior-posterior (AP); number of dynamic volume, 32; NSA, 1; and orientation, axial.

Figure 13:
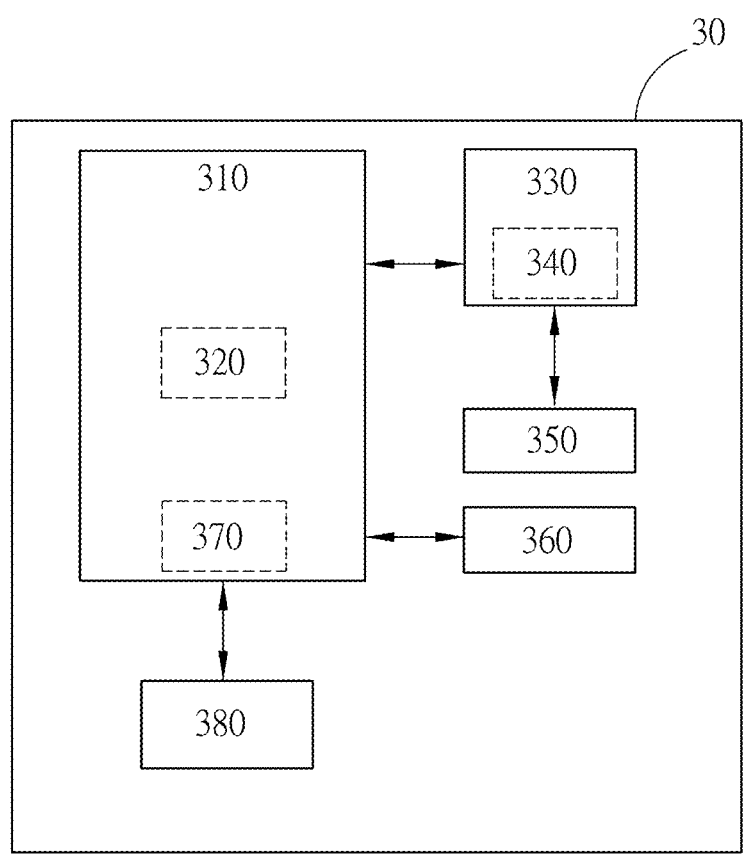
FIG. 13 is a schematic block diagram showing an image reassembly system according to the embodiment of the invention.

FIG. 13 illustrates a block diagram of an image reassembly system 30 according to an embodiment of the invention. The aforementioned method can be executed by a processing device 310 and/or a computing apparatus along with the MRI apparatus 380. The MRI apparatus 380 can comprise computer-executable instructions and/or MRI technology. Such a processing device 310 and/or computing apparatus may include a computer and/or all or a portion of the processor 320. The computer and/or processor 320 can include one or more microprocessors, utilizing instructions stored in a computer-readable storage medium, such as a hard disk, memory, flash drive, optical disc, or combinations thereof.

As shown in FIG. 13, an embodiment of the invention, a computer-readable storage medium 330, can be provided for communication with the processing device 310. The computer-readable storage medium 330 may contain executable instructions 340. Additionally, a storage device 350 can be separately provided in association with the computer-readable storage medium 330. This storage device 350 can supply instructions to the processing device 310 to execute the exemplary processes and methods as described above.

Additionally, the exemplary processing device 310 can be equipped with or include an input/output device 370, which can comprise wired networks, wireless networks, the internet, intranets, data collection probes, sensors, and the like. As shown in FIG. 13, the processing device 310 can communicate with a display device 360. In this embodiment, the display device 360 can be a touch-sensitive display panel configured not only for outputting information from the processing device but also for inputting information to the processing device. Furthermore, the display device 360 and/or the storage device 350 can be used to display and/or store data in a user-accessible and/or user-readable format.

In summary, the disclosed image reassembly system, method, and computer-readable storage medium for magnetic resonance imaging are designed to acquire the subject's self-modeled profile through the pre-scanning process. This profile is used to correct signals obtained during formal scanning. By establishing the reassembled reference state table, the system selects appropriate corresponding image volume data to generate the reassembled image volume. Notably, the reassembled reference state table represents the temporal position and respiratory state of K-space and each excitation point, offering at least the following advantages: (1) efficient search for usable excitation points; (2) easy application of predefined selection criteria, including motion states and volume selections in K-space images; and (3) clear identification of the distribution of selected excitation points in K-space.

Even though numerous characteristics and advantages of certain inventive embodiments have been set out in the foregoing description, together with details of the structures and functions of the embodiments, the disclosure is illustrative only. Changes may be made in detail, especially in matters of arrangement of parts, within the principles of the present disclosure to the full extent indicated by the broad general meaning of the terms in which the appended claims are expressed.

What is claimed is:

1. An image reassembly method applied to magnetic resonance imaging, comprising:
    a pre-scanning process, comprising:
        obtaining a pre-scan breathing curve associated with a subject from a breath detector;
        obtaining a navigator profile associated with a target tissue of the subject along a sagittal direction while obtaining a breathing curve profile;
        correcting a time difference of the pre-scan breathing curve according to a navigator profile, wherein the time difference between the pre-scan breathing curve and the navigator profile is obtained by aligning the pre-scan breathing curve and the navigator profile through peak detection; and
        generating a calibrated respiratory waveform according to the average of the pre-scan breathing curve; and
    a formal scanning process, comprising:
        obtaining a free-breathing curve associated with the subject from the breath detector, which has a plurality of respiratory waveforms;
        utilizing the calibrated respiratory waveform to refill the respiratory waveforms of the free-breathing curve for generating a free-breathing signal;
        generating a reassembled reference state table according to the free-breathing signal;
        obtaining a plurality of image volume data of the target tissue of the subject according to the reassembled reference state table; and
        retrieving the relevant image volume data based on the reassembled reference state table to generate a reassembled image volume.

2. The image reassembly method of claim 1, in the pre-scanning process, the step to obtain the calibrated respiratory waveform, comprising:
    segmenting the pre-scan breathing curve into a plurality of respiratory waveforms;
    adjusting each respiratory waveform to the same length; and
    averaging the adjusted length of respiratory waveforms to derive the calibrated respiratory waveform.

3. The image reassembly method of claim 2, wherein the respiratory waveforms are differentiated through a peak detection of the pre-scan breathing curve.

4. The image reassembly method of claim 2, wherein each respiratory waveform is adjusted in length by interpolation.

5. The image reassembly method of claim 1, wherein after obtaining the free-breathing curve, further comprising:

adjusting the timing of the free-breathing curve according to the time difference obtained by the pre-scanning process.

6. The image reassembly method of claim 1, wherein in the formal scanning process, further comprising:

normalizing the amplitude of each respiratory waveform of the free-breathing curve to a range of 0 to 1.

7. The image reassembly method of claim 1, wherein the image volume data is a K-space volume.

8. The image reassembly method of claim 1, wherein the reassembled image volume comprises a plurality of consecutive excitation points corresponding to the reassembled reference state table, and the number of excitation points is fewer than three times the count of excitation points required for composing a single reassembled image volume.

9. An image reassembly system for reassembling an image associated with a target tissue, comprising:

a computer device configured to perform the processes, comprising:

a pre-scanning process, comprising:

obtaining a pre-scan breathing curve associated with a subject from a breath detector;

obtaining a navigator profile associated with a target tissue of the subject along a sagittal direction while obtaining a breathing curve profile;

correcting a time difference of the pre-scan breathing curve according to a navigator profile, wherein the time difference between the pre-scan breathing curve and the navigator profile is obtained by aligning the pre-scan breathing curve and the navigator profile through peak detection; and generating a calibrated respiratory waveform according to the average of the pre-scan breathing curve; and a formal scanning process, comprising:

obtaining a free-breathing curve associated with the subject from the breath detector, which has a plurality of respiratory waveforms;

utilizing the calibrated respiratory waveform to refill the respiratory waveforms of the free-breathing curve for generating a free-breathing signal;

generating a reassembled reference state table according to the free-breathing signal;

obtaining a plurality of image volume data of the target tissue of the subject according to the reassembled reference state table; and retrieving the relevant image volume data based on the reassembled reference state table to generate a reassembled image volume.

* * * * *